United States Patent [19]

Nonami et al.

[11] Patent Number: 5,032,552

[45] Date of Patent: Jul. 16, 1991

[54] BIOMEDICAL MATERIAL

[75] Inventors: Tohru Nonami, Ichikawa; Nobuo Yasui, Narita, both of Japan

[73] Assignee: TDK Corporation, Tokyo, Japan

[21] Appl. No.: 374,989

[22] Filed: Jul. 3, 1989

[30] Foreign Application Priority Data

| Jul. 4, 1988 | [JP] | Japan | 63-164959 |
| Jul. 4, 1988 | [JP] | Japan | 63-164960 |
| Aug. 26, 1988 | [JP] | Japan | 63-210669 |
| Oct. 26, 1988 | [JP] | Japan | 63-268102 |
| Jan. 12, 1989 | [JP] | Japan | 1-5388 |
| Feb. 16, 1989 | [JP] | Japan | 1-34967 |

[51] Int. Cl.$^5$ .................................................. C04B 35/80
[52] U.S. Cl. .................................................. 501/95; 501/1; 106/35
[58] Field of Search ........................ 501/1.95; 106/35

[56] References Cited

U.S. PATENT DOCUMENTS

| 4,149,893 | 4/1979 | Aoki et al. | 501/123 |
| 4,503,157 | 3/1985 | Hatahira | 501/1 |
| 4,643,982 | 1/1987 | Kasuga et al. | 501/8 |
| 4,772,573 | 9/1988 | Toriyama et al. | 501/1 |

FOREIGN PATENT DOCUMENTS 0104640 4/1984 European Pat. Off. .
63-153071 12/1986 Japan .

Primary Examiner—Mark L. Bell
Assistant Examiner—Deborah Jones
Attorney, Agent, or Firm—Oblon, Spivak, McClelland, Maier & Neustadt

[57] ABSTRACT

A biomedical material for use as artificial bone and dental root is provided which takes the form of a sintered composite body comprising a crystalline calcium phosphate matrix and inorganic whiskers dispersed therein. The inorganic whiskers contain at least one oxide selected from the group consisting of silicon oxide, aluminum oxide, calcium oxide and magnesium oxide. The matrix of tricalcium phosphate or apatite preferably has a grain size of 0.05 to 30 $\mu$m. The whiskers, typically anorthite and diopside whiskers occupy 0.5 to 95% by area of a cross section of the sintered body, and preferably have a length of 0.05 to 30 $\mu$m and an aspect ratio of from 1.2 to 100, with the ratio of matrix grain size to whisker length being 10/1 to 1/10. The material has physical toughness and stength and biomedical affinity. The material is prepared by mixing calcium phosphate and a whisker-forming material or whiskers and sintering the mixture at a temperature of 800° to 1600° C.

10 Claims, 4 Drawing Sheets

BIOMEDICAL MATERIAL

This invention relates to a biomedical material in the form of a whisker-reinforced sintered body and a method for making the same. More particularly, it relates to a biomedical material for use as artificial bone and dental root in the form of a sintered body based on calcium phosphate having biological activity and affinity and reinforced with whiskers as well as a method for making the same.

BACKGROUND OF THE INVENTION

Calcium phosphate materials including hydroxyapatite, fluoroapatite, and tricalcium phosphate are widely used as living hard tissue replacements such as artificial bones and dental roots because their sintered bodies are non-toxic and likely to bond with the bone in a living system. Sintered calcium phosphate, however, is not necessarily satisfactory in practice because it is neither mechanically strong nor tough. Sintered calcium phosphate tends to break or chip away when it is shaped to a configuration conforming to a deficient site in a living system, fitted and embedded in the site.

One solution is the use of a core which is coated with calcium phosphate as disclosed in Japanese Patent Publication No. 39533/1983. However, calcium phosphate coatings do not bond firmly to the core. Japanese Patent Application Kokai No. 161971/1988 teaches to enhance the bond between a calcium phosphate coating and a core by interposing ceramics fibers having one end embedded in the core and another end protruding into the coating. Nevertheless, the strength and toughness of calcium phosphate coatings themselves are unsatisfactory.

Various mixtures were proposed in order to increase the strength of calcium phosphate. For example, Japanese Patent Publication No. 40803/1982 discloses an admixture of apatite and at least one member of particulate $SiO_2$, $Al_2O_3$, and the like. Japanese Patent Application Kokai Nos. 96359/1987 and 96360/1987 discloses a mixture of tricalcium phosphate and particulate amorphous quartz. Japanese Patent Application Kokai No. 297254/1987 discloses a mixture of calcium phosphate and particulate ceramic material. These mixtures show increased flexural strength, but are insufficient in toughness.

Japanese Patent Application Kokai No. 57971/1984 discloses fibrous or acicular apatite which is reinforced with mineral fibers. This composition, however, is impractical in that manufacture of apatite in fiber or needle form is very difficult and mineral fibers having affinity thereto must be separately prepared. It is a cumbersome operation to sinter apatite in close contact with mineral fibers under pressure at a relatively low temperature of lower than 800° C. under conditions to prevent substantial escape of moisture. In addition, such low-temperature sintering results in a low relative density. Many problems must be overcome before this composition can be used in practice.

Japanese Patent Application Kokai No. 162676/1987 discloses a composite apatite material of whisker reinforcement type in which mullite whiskers are simultaneously grown during sintering of apatite. However, this reference pays no attention to the grain size of apatite and the amount and dimensions of whiskers. More particularly, according to this reference, a reinforced composite material is prepared by mixing calcium phosphate powder and a mixture of powder silica and powder alumina as a mullite-forming material, and sintering the resulting mixture at 1300° to 1350° C. The present inventors found that when the mixture was sintered at such temperatures, whiskers precipitated only in an amount occupying less than 0.1% by area of a cross section of the sintered body. The sintered body is not tough enough to prevent cracking and chipping upon application to a deficient site in a living system.

Japanese Patent Application Kokai No. 166772/1988 discloses whisker-reinforced ceramics. Whiskers of SiC or $Si_3N_4$ are dispersed in ceramics. Examples of the ceramics disclosed therein are $Si_3N_4$, SiAlON, zirconia, alumina, and calcium phosphate. Japanese Patent Application Kokai No. 151652/1988 discloses a biomedical implanting material comprising calcium phosphate matrix and 40 to 85% by weight of the material of SiC whiskers having an average length of 2 to 10 $\mu$m. Undesirably SiC and $Si_3N_4$ whiskers have poor biological affinity.

There is a need for overcoming the above-mentioned problems of the prior art sintered calcium phosphate materials.

SUMMARY OF THE INVENTION

An object of the present invention is to provide a novel and improved biomedical material having biological activity and affinity in the form of a sintered body of whisker reinforcement type having high strength and increased toughness.

Another object of the present invention is to provide a method for making such a biomedical material.

Making efforts in search of a sintered body of whisker reinforcement type having high strength and toughness, the inventors have found that the object is achieved with crystalline calcium phosphate matrix having whiskers dispersed therein when the grain size of the matrix, and the amount, length and aspect ratio of whiskers dispersed are controlled to specific ranges.

According to the present invention, there is provided a biomedical material in the form of a sintered composite body comprising a crystalline calcium phosphate matrix and inorganic whiskers dispersed therein. The whiskers occupy 0.5 to 95% by area of a cross section of the sintered body. The whiskers contain at least one oxide selected from the group consisting of silicon oxide, aluminum oxide, calcium oxide and magnesium oxide. The matrix preferably has a grain size of 0.05 to 30 $\mu$m. The whiskers preferably have a length of 0.05 to 30 $\mu$m and an aspect ratio of from 1.2/1 to 100/1. The ratio of matrix grain size to whisker length ranges preferably from 10/1 to 1/10.

A biomedical material as defined above is prepared by mixing a calcium phosphate material and a whisker-forming material, and sintering the mixture at a sufficient temperature of 800° to 1600° C. for a sufficient time to allow whiskers to grow. Alternatively, the biomedical material is prepared by mixing a calcium phosphate material and inorganic whiskers preferably having a length of 0.05 to 30 $\mu$m and an aspect ratio of from 1/1 to 100/1, and sintering the mixture at a temperature of 800° to 1600° C.

BRIEF DESCRIPTION OF THE DRAWINGS

The above and other objects, features, and advantages of the present invention will be better understood from the following description taken in conjunction with the accompanying drawings, in which.

DETAILED DESCRIPTION OF THE INVENTION

The calcium phosphate materials used as sintering stock material in the practice of the present invention include a variety of calcium phosphate compounds, for example, tricalcium phosphate $Ca_3(PO_4)_2$, and apatite series calcium phosphates $Ca_{10}(PO_4)_6X_2$ wherein X is OH, halogen (e.g., fluoro and chloro), $CO_3$ or the like, such as hydroxyapatite, fluoroapatite, chloroapatite, and carbonated apatite. They may be used alone or in admixture of two or more.

Preferred calcium phosphates are of the apatite series, especially hydroxyapatite and fluoroapatite. These apatites may be either synthetic apatites prepared by dry and wet processes or biotic apatites collected from bones and teeth of various vertebrate animals. A typical dry synthetic process is by reacting calcium phosphate with excess CaO in a steam stream at a high temperature of 900° to 1300° C.

The preferred calcium phosphate materials used herein are apatites, especially hydroxyapatites and fluoroapatites, having an atomic calcium to phosphorus (Ca/P) ratio of from 165/100 to 175/100. Hydroxyapatites are most preferred.

Also fluoroapatites have many advantages. They do not convert into $\beta$-tricalcium phosphate or $\alpha$-tricalcium phosphate upon sintering. They are highly stable, strong, and tough because they are free of strains due to shrinkage or expansion. They are resistant to corrosion and acid.

If the Ca/P atom ratio is less than 165/100, there is some likelihood that part of whiskers, whisker-forming material or reinforcing additives (such as SiO, $Al_2O_3$, and MgO) would form a solid solution with the apatite, inducing a change in the composition of whiskers. As a result, whiskers might not fully precipitate. In the case of hydroxyapatite, part of whisker components might form a solid solution with the apatite to form tricalcium phosphate, inducing strains and losing strength and biological affinity.

The hydroxyapatites are generally microporous. They may have pores with a diameter of 5 to 200 μm and a porosity of 20 to 50%.

The preferred tricalcium phosphate used herein is $\alpha$-tricalcium phosphate although $\beta$-tricalcium phosphate may be used. Also a mixture of porous hydroxyapatite and tricalcium phosphate may be used.

These calcium phosphate materials are used in the form of powder having a particle size of 0.1 to 1000 μm or granules having a particle size of 0.1 to 3 mm. The powder or granules preferably have a surface area of about 0.01 to 300 m²/g in BET value.

In the practice of the invention, the above-mentioned calcium phosphate materials should be eventually sintered into crystalline calcium phosphate having a grain size of 0.05 to 30 μm, preferably 0.1 to 20 μm, more preferably 0.1 to 10 μm. A grain size smaller than the lower limit is difficult to achieve whereas a grain size larger than the upper limit results in a reduced strength.

The inorganic whiskers, more precisely inorganic oxide whiskers contain at least one oxide selected from the group consisting of silicon oxide (silica), aluminum oxide (alumina), calcium oxide (calcia), and magnesium oxide (magnesia) because whiskers otherwise show poor biological affinity. Better biological affinity and activity are achievable when the inorganic oxide whiskers contain at least two oxides selected from the group consisting of silicon oxide (silica), aluminum oxide (alumina), and calcium oxide (calcia), and contain optionally magnesium oxide (magnesia), especially when the inorganic oxide whiskers contain i) silicon, ii) calcia and iii) alumina and/or magnesia.

The inorganic whiskers are preferably selected from the group consisting of alumina whiskers, calcium silicate whiskers, aluminum silicate whiskers, aluminum silicate calcium whiskers, calcium silicate magnesium whiskers, calcium aluminate whiskers, and magnesium silicate whiskers.

Because of biological activity and biological affinity or compatibility, preferred are alumina whiskers, aluminum silicate calcium whiskers such as anorthite ($CaO.2SiO_2.Al_2O_3$) whiskers, calcium silicate magnesium whiskers such as diopside ($CaO.2SiO_2.MgO$) whiskers, and calcium silicate whiskers such as wollastonite ($CaO.SiO_2$) whiskers. Among them, anorthite whiskers and diopside whiskers are most preferred because of outstandingly high biological activity. The whiskers may have a composition deviating more or less from the stoichiometry as shown above.

The inorganic whiskers are generally used in an amount of about 0.5 to about 95 percent by weight, preferably about 5 to about 70 percent by weight, more preferably about 10 to about 60 percent by weight per 100 parts by weight of sintering body. If inorganic whiskers are used in more amounts beyond the range, the desirable properties of calcium phosphate, for example, the biological affinity of apatite as artificial bone are reduced or lost. Materials containing less amounts of inorganic whiskers will result in sintered bodies having low mechanical strength (e.g., bending strength) and toughness. It will be understood that when pre-formed whiskers are used, the whiskers in the resulting sintered body have approximately the same dimensions as the original.

Whisker-forming materials, that is, materials which can convert into whiskers under sintering conditions may also be used, for example, silica, calcium oxide, magnesium oxide, and alumina, as well as those which can convert into these compounds upon sintering, such as corresponding carbonates, bicarbonates, and hydroxides. These materials may be used in the form of powder, granules, slurry, and aqueous solution. The materials in the form of powder or granules preferably have a BET value of about 0.01 to about 300 m²/g.

These whisker-forming materials may be blended in such a proportion corresponding to the composition of the desired whiskers. Useful are a blend comprising a silica source in an amount of 0.05 to 600 parts by weight of $SiO_2$ and a calcium oxide source in an amount of 0.05 to 600 parts by weight of CaO or an alumina source in an amount of 0.05 to 600 parts by weight of $Al_2O_3$; and a blend comprising a silica source in an amount of 0.05 to 800 parts by weight of $SiO_2$, a calcium oxide source in an amount of 0.05 to 600 parts by weight of CaO, and at least one of an alumina source in an amount of 0.05 to 600 parts by weight of Al$_2$O$_3$ and a magnesia source in an amount of 0.05 to 600 parts by weight of MgO, all parts being per 100 parts by weight of the calcium phosphate material. In the latter case, the sources may be blended in such proportions that 0.5 to 20 mol of silica, 0.1 to 20 mol of alumina and 0.1 to 20 mol of magnesia are present per mol of calcium oxide.

In addition, one or more of zirconia, strontium oxide, and barium oxide sources may be used in sufficient amounts to provide up to 20 parts by weight of ZrO$_2$, SrO, and BaO on the same basis as above.

When it is desired to grow diopside whiskers, for example, the sources may be blended in such proportions that 0.15 to 14 mol, preferably 0.5 to 5 mol, more preferably 0.8 to 2.5 mol, most preferably 0.8 to 1.2 mol of magnesium oxide and 0.5 to 10 mol, preferably 2 to 5 mol, more preferably 2 to 3 mol, most preferably 2 to 2.5 mol of silica are present per mol of calcium oxide.

When it is desired to grow anorthite whiskers, for example, the sources may be blended in such proportions that 0.1 to 20 mol, preferably 0.2 to 1.5 mol, more preferably 0.8 to 1.2 mol of alumina and 1 to 10 mol, preferably 2 to 5 mol, more preferably 2 to 3 mol, most preferably 2 to 2.5 mol of silica are present per mol of calcium oxide.

These sources may be added individually to the calcium phosphate component or previously admixed in a proportion as described above and sintered at 600° to 1600° C. before addition. Instead of individual addition, it is also possible to add a component capable of forming whiskers, for example, a diopside component corresponding to composition CaO.2SiO$_2$.MgO and an anorthite component corresponding to composition CaO.2-SiO$_2$.Al$_2$O$_3$. These components may also be used in powder or granule form like the calcium phosphate component. The whisker-forming components in powder form preferably has a BET value of about 0.01 to about 300 m$^2$/g.

A mixture of two types of stock materials, a calcium phosphate-forming component and a whisker or whisker-forming component as described above, is sintered into a sintered composite body consisting essentially of 5 to 95% by weight of crystalline calcium phosphate and 95 to 5% by weight of whiskers (typically, diopside or anorthite). The presence of matrix and whisker by-products created upon sintering is permitted as long as the desired effect is not impaired. In the examples mentioned above, permissible is inclusion of such by-products as α-tricalcium phosphate and other oxides such as forsterite and wallastonite in the case of diopside whiskers and akermanite and mullite in the case of anorthite whiskers. The by-products are usually copresent in the matrix.

In the case of forming whiskers upon sintering, the whisker-forming material preferably has a sintering temperature higher by 50° to 400° C. than the sintering temperature of the calcium phosphate material. Source materials as described above may be readily blended so as to give such a sintering temperature. The sintering temperature of a material can be readily determined by measuring an increase of shrinkage factor using a thermodilatometer.

In the sintered composite body, the calcium phosphate forming the matrix is present as crystals and the whiskers are dispersed in the matrix.

The whiskers each have a length and a diameter. The whisker length is in the range of from 0.05 to 30 μm, preferably from 0.2 to 30 μm, more preferably from 0.2 to 15 μm. The aspect ratio defined as length divided by diameter is in the range of from 1.2/1 to 100/1, preferably from 1.5/1 to 100/1, more preferably from 2/1 to 20/1, most preferably from 3/1 to 15/1. Shorter whiskers outside the length range are less effective whereas longer whiskers tend to induce strain. Whiskers having an aspect ratio of less than 1 are less effective whereas whiskers having an aspect ratio of more than 100 tend to induce strain.

The ratio of matrix grain size to whisker length is in the range of from 10/1 to 1/10, preferably from 14/10 to 2/10, more preferably from 1/1 to 2/10. If the ratio is smaller than 1/10, strains are induced upon sintering, losing strength. If the ratio is larger than 10/1, the whiskers do not fully exert their function of increasing strength.

The whiskers occupy 0.5 to 95% by area, preferably 5 to 75% by area, more preferably 10 to 60% by area of a cross section of the sintered body. Outside the range, sintered bodies having less amounts of whiskers are less tough whereas sintered bodies having excess amounts of whiskers are low in biological affinity. The percent area that whiskers occupy in a cross section of the sintered body can be determined using a photomicrograph. More particularly, a sintered body sample is sectioned. The section is mirror polished, and then chemically etched with aqueous 1–5% HCl or thermally etched at a temperature of higher than 800° C., but lower than the whisker forming temperature. The section is then observed under a scanning electron microscope. The photomicrograph is then transferred to a section paper, from which the percent area of whiskers is calculated by counting the corresponding sections. The procedure may be repeated five times, for example, determining the percent area of whiskers.

The preparation of the biomedical material of the present invention will be described in detail. The starting material is powder calcium phosphate material. A predetermined amount of whiskers or whisker-forming materials in powder form is added to the powder calcium phosphate material along with a dispersant. The whisker-forming materials are materials that can transform into whiskers under sintering conditions, for example, silica, calcium oxide, magnesium oxide, and alumina, and may be added separately or as a premix. Use of sources which produce materials that can together form whiskers under sintering conditions is also contemplated. Materials having whisker compositions such as the anorthite and diopside compositions are also useful.

The dispersant assists in uniformly dispersing whiskers or whisker-forming materials in powder calcium phosphate material. Examples of the dispersant include anionic surface-active agents such as carboxylate salts and sulfonate salts.

The thus prepared powder mixture is shaped into a desired shape by a conventional method such as press molding and slip casting, dried, and then sintered in air at a temperature of 800° to 1600° C. Shaping is generally carried out under a pressure of 1 to 10,000 kg/cm$^2$.

Sintering is preferably effected at a temperature of 800° to 1500° C. particularly when it is desired to form anorthite whiskers. Sintering is preferably effected at a temperature of 900° to 1500° C. particularly when it is desired to form diopside whiskers. When pre-formed whiskers are used, sintering may be effected at a temperature of 800° to 1600° C. The sintering time generally ranges from about 5 minutes to about 15 hours in either case.

Sintering creates crystalline calcium phosphate matrix or crystalline calcium phosphate matrix and whiskers at the same time when the whisker-forming material is used. There is obtained a sintered composite body in which whiskers are dispersed in the crystalline calcium phosphate matrix, both the matrix and whiskers meeting the dimensional requirements. The sintered composite body is useful as biomedical material.

As compared with the addition of pre-formed whiskers, it is advantageous to form whiskers simultaneous with crystalline calcium phosphate as the matrix because the resulting sintered body has improved toughness and strength due to the increased bond between the whiskers and the matrix.

When diopside whiskers free of alumina are formed, the material mixture can be sintered at a temperature in a wide range of 900° to 1500° C. without the risk of conversion of hydroxyapatite into tricalcium phosphate or β-tricalcium phosphate into α-calcium phosphate catalyzed by alumina. Formation of anorthite whiskers also avoids such a risk because they can be formed at temperatures of lower than 1300° C.

When the sintering temperature is set to lower than 1300° C. in the above-defined range, a sintered body having good biological affinity and mechanical strength and toughness can be obtained even from hydroxyapatite prepared by a wet process without causing abnormal grains to grow.

The formation of whiskers during sintering is described in further detail. When the whisker-forming material or mixture used has a sintering temperature higher by 50° to 400° C. than the sintering temperature of the calcium phosphate material as previously described, the calcium phosphate is sintered in an earlier stage where the whisker component has not been activated. Consequently, the whisker component is unlikely to diffuse into the matrix in this stage. If diffusion occurs in this stage, then the respective components would change their composition with a possibility that little whiskers would form or glass would form. Such a risk is avoided by controlled diffusion of the whisker component in the early stage. Whiskers start precipitating in a later stage when calcium phosphate has been sintered to a certain extent. A practically satisfactory density is achieved without any problems that whiskers having the matrix component included therein can precipitate and that no sufficient density is available because the matrix has not been fully sintered when formation of whiskers is complete. In addition, there are little possibilities that the matrix is sintered too earlier than necessary, and premature sintering of the matrix prevents whiskers from precipitating or causes precipitating whiskers to be largely stressed.

Better results are obtained when an intermediate layer is present between grains of the crystalline calcium phosphate matrix and inorganic whiskers. The intermediate layer extends partially or entirely along the boundary therebetween. The intermediate layer contains at least one of the elements in either one or both of the whiskers and the matrix. Since some elements like calcium are common to both the whiskers and the matrix, the intermediate layer preferably contains the common element or elements. The intermediate layer has a continuous or stepwise gradient of concentration between the whiskers and the matrix grains. More illustratively, for one element contained in the whisker, the intermediate layer contains the element in a high concentration adjacent the whisker and gradually reduces its concentration toward the interface with the matrix.

The intermediate layer generally has a thickness of up to 3 μm, preferably from 0.005 to 3 μm, more preferably from 0.01 to 1.5 μm, most preferably from 0.05 to 1.0 μm.

The intermediate layer may be formed by slowly cooling down the sintered body from the sintering temperature over an extended time. Cooling is preferably performed at a slow constant rate of 0.2° to 30° C./min., more preferably 0.5° to 10° C./min.

Provision of an intermediate layer between whiskers and grains prevents direct reaction between whiskers and grains so that the whiskers are no longer changed maintaining sufficient strength, improves the bond between whiskers and grains also contributing to strength, and enables easy control of the interface between whiskers and grains. As a result, the sintered body is reinforced more densely, further improving mechanical strengths such as flexural strength and toughness.

Orientation of whiskers in the matrix is possible and desirable because the strength of the biomedical material is improved. Preferably, the whiskers are present in the matrix at a degree of orientation of at least 60%, more preferably at least 75%, most preferably at least 85%.

Whiskers may be oriented by adding a binder to a blend of a calcium phosphate material and whiskers and milling the mixture. The binder used herein may be selected from those commonly used for biomedical materials, for example, rubber or thermoplastic resins. The binder may be added to the blend in amounts commonly used for biomedical materials, generally in amounts of 10 to 50%, preferably 20 to 45% by weight of the blend. Less amounts of binder are ineffective in helping orientation whereas larger amounts of binder would result in porous sintered bodies which are low in biological affinity and density.

Next, it is necessary to process the mixture so as to have a controlled degree of orientation of whiskers of 60% or higher. In practice, the mixture is repeatedly rolled to control the degree of orientation. The rolling process renders whiskers anisotropic. Sufficient orientation may be accomplished by repeating the rolling step several times, for example, 3 to 10 times. The rolling process includes rolling techniques such as calendering, pressing and extrusion techniques. Rolling techniques are preferred. The pressure under which the mixture is rolled is generally in the range of from 20 to 300 kg/cm$^2$, preferably from 50 to 150 kg/cm$^2$. Lower rolling pressures would be ineffective to provide sufficient strength whereas higher rolling pressures give no further benefits.

The mixture is thus rolled into a plate or sheet material, which is sintered into a sintered body with or without post-processing like hot pressing before sintering.

There is thus obtained a biomedical material in the form of a sintered body of a crystalline calcium phosphate matrix having whiskers dispersed therein. The composite material is improved in many respects while the desired properties of calcium phosphate material, for example, the biological affinity of apatite as artificial bone is maintained. The strength of the composite material is increased by controlling the grain size of the matrix to a specific range. Occurrence of strain during sintering is minimized by controlling the dimensions of whiskers, that is, the length and aspect ratio of whiskers and the ratio of matrix grain size to whisker length to specific ranges. A desirable amount of whiskers can be distributed in the matrix along the grain boundaries or among grains without localization, preventing cracking. Growth of whiskers can be delayed relative to matrix sintering to produce a sintered body having improved toughness and fracture energy.

Since the sintered body of the invention has high strength and toughness as well as biological affinity and activity, it can find application as artificial bone, dental root and joint materials for treatments in orthopaedic surgery, dental and oral surgery.

An advantage of the method of the invention is that high strength and toughness can be readily and efficiently imparted to a biomedical material.

EXAMPLE

Examples of the present invention are given below by way of illustration and not by way of limitation.

EXAMPLE 1

As reported in Table 1, hydroxyapatite (HAP) and whisker-forming material were milled along with a dispersant in a ball mill for one hour. The slurry was filtered through a qualitative filter paper. The collected cake was dried at 120° C. for 5 hours and a 50-gram portion of the cake was then molded in a mold of 40 mm by 50 mm under a pressure of 300 kg/cm$^2$. The molded material was sintered at the temperature shown in Table 1 for 2 hours, obtaining a sintered body useful as biomedical material.

The hydroxyapatites used had an atomic calcium-to-phosphorus (Ca/P) ratio of 1.67 and the BET values shown in Table 1.

The whisker-forming materials used were anorthites and diopsides having the BET values shown in Table 1. The amount of whisker-forming material added is reported in Table 1 in % by weight based on the total weight of HAP plus whisker-forming material. The whisker-forming materials used are as identified below.

Anorthite A: sintered $CaO \cdot Al_2O_3 \cdot 2SiO_2$
Anorthite B: a mixture of $SiO_2$ 61% by weight, $Al_2O_3$ 17% by weight, and CaO 22% by weight
Anorthite C: a mixture of $SiO_2$ 50% by weight, $Al_2O_3$ 30% by weight, and CaO 20% by weight
Diopside A: sintered $CaO \cdot MgO \cdot 2SiO_2$
Diopside B: a mixture of $SiO_2$ 61% by weight, MgO 12% by weight, and CaO 27% by weight
Diopside C: a mixture of $SiO_2$ 55% by weight, MgO 19% by weight, and CaO 26% by weight The BET values of anorthites B and C and diopsides B and C are those of mixtures of necessary ingredients.

The dispersant was SN Dispersant 5045 manufactured and sold by SAN NAPCO Limited and was used in an amount of 0.05% by weight based on the total weight of HAP plus whisker-forming material.

The thus obtained biomedical materials were sectioned and observed under an electron microscope to determine their whisker amount, matrix grain size (D), whisker length (L), whisker aspect ratio, and matrix grain size/whisker length ratio (D/L). They were also measured for relative density, flexural strength (F.S.), and toughness ($K_IC$). The results are shown in Table 2.

Measurement of relative density, flexural strength, and toughness ($K_IC$) is as described below.

Relative density (porosity)

The density of a sintered sample was measured by the Archimedian method. The sintered sample was pulverized into powder having a surface area of 5 m$^2$/g which was measured for true density. Relative density was calculated from the apparent and true densities.

Flexural strength (F.S.)

Ten test specimens of $3 \times 4 \times 40$ mm were cut out and mirror polished. They were measured by the three point bending test with a span of 36 mm and a cross head speed of 0.5 mm/min.

Fracture toughness ($K_IC$)

Fracture toughness was measured according to ASTM E399-83.

Comparative samples outside the scope of the invention are also reported in Tables 1 and 2.

Figure 1:
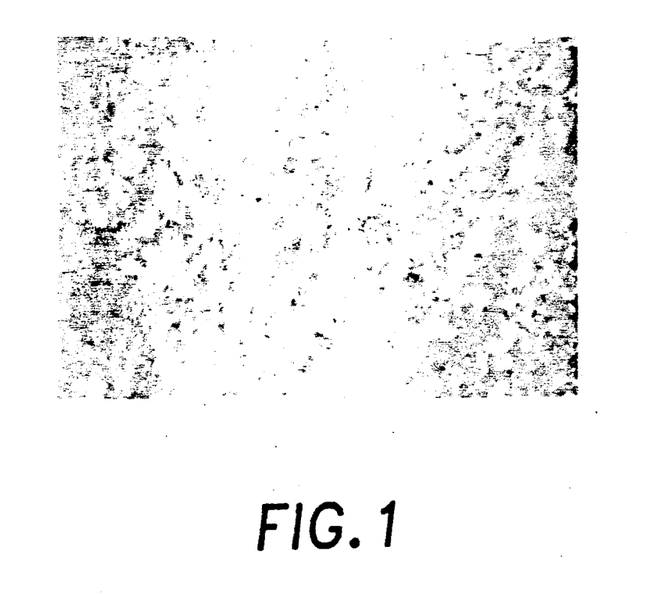
FIGS. 1 and 2 are photomicrographs under a scanning electron microscope of biomedical material sample Nos. 2 and 3 in Example 1, respectively.
Figure 2:
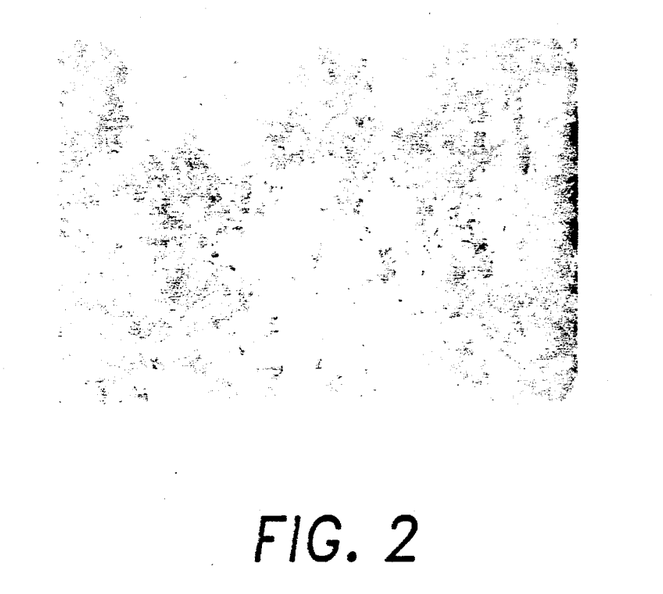

FIGS. 1 and 2 are photomicrographs of sample No. 2 containing diopside whiskers and sample No. 3 containing anorthite whiskers, both taken under a scanning electron microscope. As seen from the photos, the sintered body has a structure in which anorthite or diopside whiskers are dispersed among hydroxyapatite grains.

Figure 3:
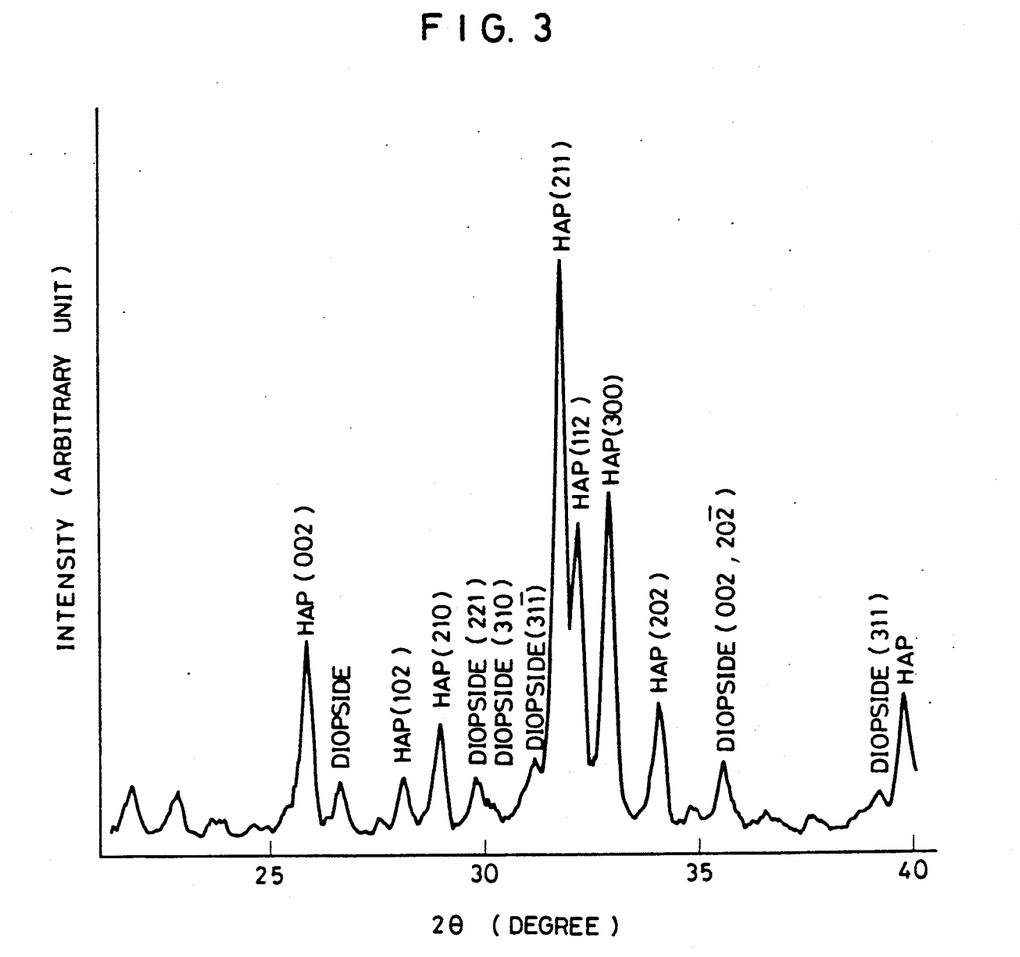
FIGS. 3 and 4 are diagrams of X-ray diffraction analysis of biomedical material sample Nos. 2 and 3 in Example 1, respectively.
Figure 4:
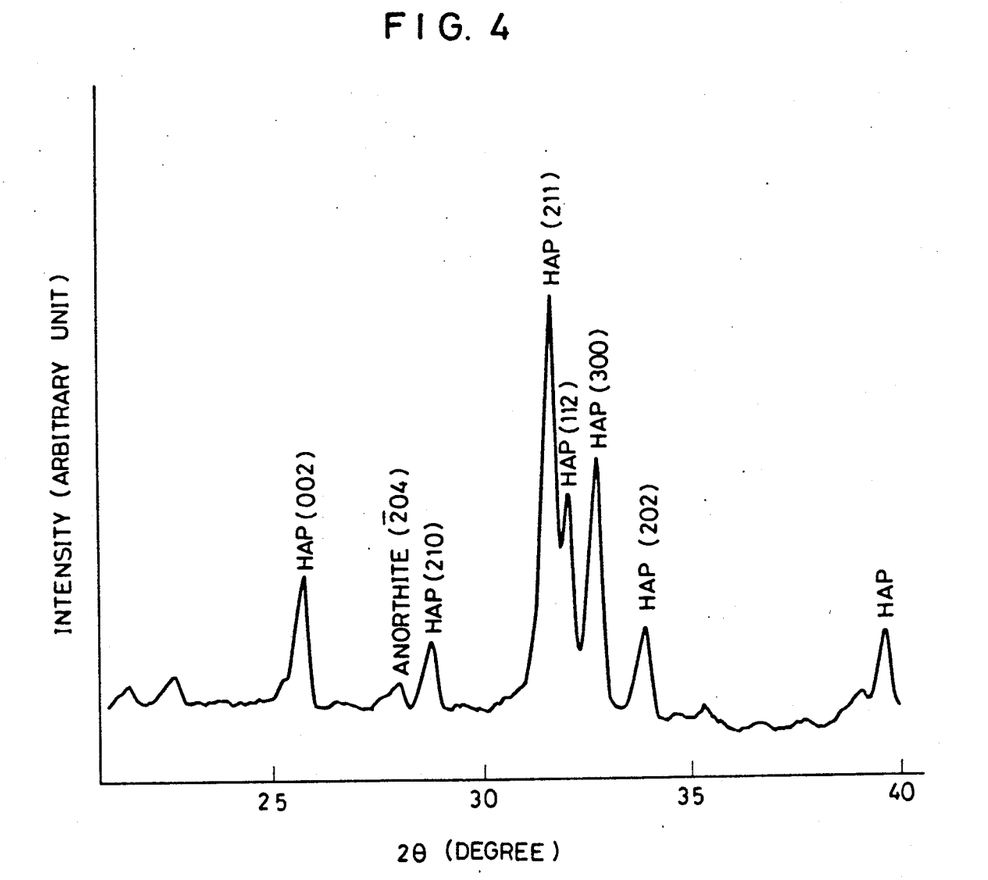

FIGS. 3 and 4 are X-ray diffraction diagrams of sample Nos. 2 and 3, indicating that diopside or anorthite whiskers are formed in hydroxyapatite.

TABLE 1

| Sample No. | HAP BET (m$^2$/g) | Whiskers Material | Amount (wt %) | BET (m$^2$/g) | Sintering Temp. (°C.) |
|---|---|---|---|---|---|
| 1 | 80 | Anorthite A | 20 | 5 | 1220 |
| 2 | 20 | Diopside A | 20 | 10 | 1250 |
| 3 | 80 | Anorthite B | 20 | 8 | 1250 |
| 4 | 15 | Diopside B | 20 | 10 | 1270 |
| 5 | 80 | Anorthite C | 20 | 15 | 1180 |
| 6 | 20 | Diopside C | 20 | 15 | 1220 |
| 7 | 80 | Anorthite A | 20 | 30 | 1160 |
| 8 | 30 | Diopside A | 20 | 30 | 1200 |
| 9 | 80 | Diopside A | 40 | 30 | 1220 |
| 10 | 80 | Diopside A | 60 | 30 | 1240 |
| 101* | 3 | Diopside A | 20 | 5 | 1300 |
| 102* | 7 | Diopside B | 20 | 5 | 1300 |
| 103* | 65 | Diopside C | 20 | 5 | 1200 |
| 104* | 70 | Diopside A | 20 | 4 | 1230 |
| 105* | 70 | Diopside A | 1 | 4 | 1200 |
| 106* | 70 | Anorthite A | 2 | 4 | 1200 |

*Comparison

TABLE 2

| Sample No. | Whisker content (area %) | Matrix grain size (μm) | Whisker length (μm) | Whisker aspect ratio | D/L | Relative density (%) | F.S. (MPa) | $K_1C$ (MPa $\sqrt{m}$) |
| --- | --- | --- | --- | --- | --- | --- | --- | --- |
| 1 | 10 | 4 | 6 | 7 | 0.67 | 99.5 | 140 | 1.3 |
| 2 | 10 | 4 | 13 | 11 | 0.3 | 99.5 | 160 | 1.4 |
| 3 | 15 | 3 | 13 | 13 | 0.23 | 99.5 | 190 | 1.9 |
| 4 | 15 | 5 | 14 | 15 | 0.35 | 99.5 | 180 | 1.9 |
| 5 | 17 | 0.3 | 0.5 | 8 | 0.6 | 99.0 | 200 | 1.8 |
| 6 | 17 | 5 | 4 | 3 | 1.25 | 99.5 | 220 | 1.8 |
| 7 | 18 | 0.3 | 0.3 | 11 | 1.0 | 99.5 | 220 | 2.5 |
| 8 | 18 | 1 | 2 | 10 | 0.5 | 99.8 | 230 | 2.8 |
| 9 | 35 | 0.5 | 2 | 15 | 0.25 | 99.9 | 290 | 3.3 |
| 10 | 45 | 0.7 | 2 | 15 | 0.35 | 99.5 | 320 | 3.6 |
| 101* | 10 | 8 | 40 | 18 | 0.2 | 88 | 60 | 0.8 |
| 102* | 15 | 8 | 40 | 18 | 0.2 | 95 | 85 | 0.9 |
| 103* | 18 | 3 | 40 | 4 | 0.07 | 99.8 | 100 | 0.8 |
| 104* | 10 | 4 | 50 | 5 | 0.08 | 99.5 | 90 | 0.9 |
| 105* | 0.1 | 4 | 6 | 7 | 0.67 | 99.7 | 100 | 0.6 |
| 106* | 0.2 | 4 | 13 | 11 | 0.3 | 99.7 | 100 | 0.6 |

*Comparison

As seen from Tables 1 and 2, the sintered bodies of the invention have improved density, strength and toughness.

Sample Nos. 1 to 10 within the scope of the invention were determined for biological activity by immersing them in simulative body fluid for several days and thereafter examining them at intervals by SEM photomicrographic observation and chemical analysis to see whether HAP precipitated on the sample surface.

An HAP layer precipitated on the surface after 3 days in the samples using diopside whiskers and after 10 days in the samples using anorthite whiskers, indicating high biological activity. Generally speaking, in order that an implant bond to the adjoining bone in the living body, it is essential that an HAP layer analogous to the natural bone form on the surface of the implant. Therefore, the samples of the invention exhibited good biological activity in this sense.

EXAMPLE 2

As reported in Table 3, hydroxyapatite (HAP) powder and alumina whiskers were milled along with a dispersant in a ball mill for one hour. The slurry was filtered through a qualitative filter paper. The collected cake was dried at 120° C. for 5 hours and then molded in a mold of 40 mm by 50 mm under a pressure of 200 kg/cm². The molded material was sintered at a temperature of 1350° C. for 2 hours, obtaining a sintered body useful as biomedical material.

The hydroxyapatite powder used had a BET value of 7 m²/g. The alumina whiskers used had a length of 2 μm and an aspect ratio of 10. The dispersant, SN Dispersant 5045 (SAN NAPCO Limited), was used in an amount of 0.05% by weight based on the total weight of HAP plus whiskers.

The sintered bodies were measured for flexural strength (F.S.) and fracture toughness ($K_fC$) as in Example 1.

The results are shown in Table 3.

TABLE 3

| Sample No. | HAP BET (m²/g) | Whisker Material | Whisker Length (μm) | Whisker Aspect ratio (μm) | Whisker Amount added (wt %) | Dispersant (wt %) | Sintering Temp. (°C.) | Matrix grain size (μm) | Whisker content (area %) | F.S. (MPa) | $K_1C$ (MPa $\sqrt{m}$) |
| --- | --- | --- | --- | --- | --- | --- | --- | --- | --- | --- | --- |
| 10 | 7 | Alumina | 2 | 10 | 5 | 0.05 | 1350 | 2 | 6 | 110 | 1.0 |
| 11 | 7 | Alumina | 2 | 10 | 10 | 0.05 | 1350 | 2 | 10 | 120 | 1.2 |
| 12 | 7 | Alumina | 2 | 10 | 20 | 0.05 | 1350 | 2 | 19 | 160 | 1.3 |
| 13 | 7 | Alumina | 2 | 10 | 50 | 0.05 | 1350 | 2 | 55 | 180 | 1.7 |

Matrix grain size/Whisker length = 1.0
Relative density = 99.0%

EXAMPLE 3

Sintered bodies were prepared by the same procedure as Sample No. 12 of Example 2 except that the whiskers were replaced by the following. These sintered bodies were found equivalent to sample No. 12.

Whisker A:
 Material: calcium silicate $CaO.SiO_2$
 Length: 3 μm
 Aspect ratio: 5

Whisker B:
 Material: aluminum silicate
 Length: 2 μm
 Aspect ratio: 5

Whisker C:
 Material: calcium aluminate
 Length: 2 μm
 Aspect ratio: 15

Whisker D:
 Material: magnesium silicate
 Length: 2 μm
 Aspect ratio: 8

Blocks of 3×4×5 mm were prepared from the samples of Examples 1 to 3. A cut-out was artificially engraved in the lower edge of the jaw bone of adult rabbits. Each block was implanted in the cut-out in the rabbit's jaw. The rabbits were killed every week after the implanting operation. Polished, but non-decalsified specimens were prepared from the implanted jaw bone. A SEM photomicrograph was taken on the interface between the implant and the newly grown bone.

The sample of Example 1 exhibited good biological activity and affinity because a direct bond was observed between the bone and the HAP after 2 weeks when diopside whiskers were used, and after 3 weeks when anorthite whiskers were used. The samples of Example 2 and 3 also exhibited good biological affinity because the bone bonded to the HAP via a thin soft tissue.

EXAMPLE 4

As reported in Table 4, hydroxyapatite (HAP) powder and whisker-forming material were milled along with a dispersant in a ball mill for one hour. The slurry was filtered through a qualitative filter paper. The collected cake was dried at 120° C. for 5 hours and a 50-gram portion of cake was then molded in a mold of 40 mm by 50 mm under a pressure of 300 kg/cm$^2$. The molded material was sintered at the temperature shown in Table 4 for 2 hours, obtaining a sintered body useful as biomedical material.

The hydroxyapatites used had varying atomic calcium-to-phosphorus (Ca/P) ratios. The whisker-forming material was Diopside A identified in Example 1. The dispersant, SN Dispersant 5045, was used in an amount of 0.05% by weight based on the total weight of HAP plus whisker-forming material.

The thus obtained biomedical materials were sectioned and observed under an electron microscope to determine their whisker amount, matrix grain size (D), whisker length (L), whisker aspect ratio, and matrix grain size/whisker length ratio (D/L). They were also measured for relative density, flexural strength (F.S.), and toughness ($K_IC$). The results are shown in Table 5.

TABLE 4

| | HAP | | Whisker | | | Sintering | |
|---|---|---|---|---|---|---|---|
| No. | BET (m$^2$/g) | Ca/P (atom ratio) | Material | Amount added (wt %) | BET (m$^2$/g) | Temp. (°C.) | Dispersant (wt %) |
| 21 | 60 | 1.67 | Diopside A | 20 | 30 | 1250 | 0.05 |
| 22 | 60 | 1.71 | Diopside A | 20 | 30 | 1250 | 0.05 |
| 23 | 60 | 1.63 | Diopside A | 20 | 30 | 1250 | 0.05 |

TABLE 5

| No. | Whisker content (area %) | Matrix grain size (μm) | Whisker length (μm) | Aspect ratio | D/L | Relative density (%) | F.S. (MPa) | $K_IC$ (MPa $\sqrt{m}$) |
|---|---|---|---|---|---|---|---|---|
| 21 | 15 | 2 | 2 | 8 | 1 | 99.8 | 250 | 2.7 |
| 22 | 15 | 2 | 2 | 8 | 1 | 99.8 | 240 | 2.7 |
| 23 | 0.1 | 2 | 3 | 8 | 0.67 | 99.8 | 100 | 0.8 |

As seen from Table 5, biomedical material sample Nos. 21 and 22 using hydroxyapatite having a Ca/P ratio of higher than 1.65 had higher flexural strength and toughness than sample No. 23 using hydroxyapatite having a Ca/P ratio of lower than 1.65 because more whiskers precipitated in the former.

EXAMPLE 5

To calcium fluorophosphate powder having a surface area of 20 m$^2$/g in BET were added 5% by weight of powder CaO, 7% by weight of powder Al$_2$O$_3$, and 12% by weight of granular SiO$_2$, based on the weight of the calcium phosphate powder. The mixture was fully mixed. A vibratory mill was charged with 100 grams of the mixture and 300 grams of water along with 1 kg of zirconia milling medium and operated for 60 minutes for milling. The contents were filtered and the collected cake was dried at 110° C. for 60 minutes. The mixture was passed through a 110-mesh screen, placed in a mold cavity of 40×50×10 mm, and press molded under a pressure of 300 kg/cm$^2$. For every two moldings, one was sintered at 1200° C. for 2 hours and the other sintered at 1300° C. for 2 hours.

Test specimens of 3×4×36 mm were prepared from these two anorthite whisker-reinforced composite sintered bodies. They were measured for flexural strength as in Example 1. The sample sintered at 1200° C. showed a flexural strength of 130 MPa and a relative density of 95.0% whereas the other sample sintered at 1300° C. showed a flexural strength of 220 MPa and a relative density of 99.7%.

Separately, samples were prepared and measured for flexural strength by the same procedures as above except that the calcium fluorophosphate was replaced by hydroxyapatite. The sample sintered at 1200° C. showed a flexural strength of 100 MPa and a relative density of 96.0% whereas the other sample sintered at 1300° C. showed a flexural strength of 150 MPa and a relative density of 99.5%.

EXAMPLE 6

To calcium fluorophosphate powder were added 4% by weight of powder CaO, 4% by weight of powder MgO, and 12% by weight of granular SiO$_2$, based on the weight of the calcium phosphate powder. Sintered bodies were prepared from this mixture by following substantially the same procedure as in Example 5. They were diopside/wallastonite whisker-reinforced composite sintered bodies.

Test specimens of 3×4×36 mm were prepared from the two bodies sintered at different temperatures and measured for flexural strength The sample sintered at 1200° C. showed a flexural strength of 140 MPa and a relative density of 94.0% whereas the other sample sintered at 1300° C. showed a flexural strength of 200 MPa and a relative density of 99.1%.

Separately, samples were prepared and measured for flexural strength by the same procedures as above except that the calcium fluorophosphate was replaced by hydroxyapatite. The sample sintered at 1200° C. showed a flexural strength of 130 MPa and a relative density of 94.0% whereas the other sample sintered at 1300° C. showed a flexural strength of 180 MPa and a relative density of 99.0%.

EXAMPLE 7

A series of sintered bodies were prepared by repeating the procedure of Example 1 while varying the cooling rate after sintering as shown in Table 6.

The samples were observed under a scanning electron microscope to find a grain boundary vitreous phase having the thickness shown in Table 7.

TABLE 6

| Sample No. | HAP BET (m²/g) | Whisker material | Amount of Whisker material added (wt %) | Sintering Temp. (°C.) | Cooling rate (°C./min) |
|---|---|---|---|---|---|
| 31 | 80 | Diopside | 20 | 1220 | 20 |
| 32 | 80 | Diopside | 20 | 1220 | 10 |
| 33 | 80 | Diopside | 20 | 1220 | 5 |
| 34 | 80 | Diopside | 20 | 1220 | 1 |
| 35 | 10 | Anorsite | 20 | 1280 | 20 |
| 36 | 10 | Anorsite | 20 | 1280 | 10 |
| 37 | 10 | Anorsite | 20 | 1280 | 5 |
| 38 | 10 | Anorsite | 20 | 1280 | 1 |
| 39* | 80 | Diopside | 20 | 1220 | 40 |

*Comparison

TABLE 7

| Sample No. | Whisker content (area %) | Matrix grain size (μm) | Whisker length (μm) | Aspect ratio | Grain boundary viscosus phase thickness (μm) | Relative density | F/S (MPa) | $K_IC$ (MPa $\sqrt{m}$) |
|---|---|---|---|---|---|---|---|---|
| 31 | 18 | 5 | 10 | 18 | 0.05 (Slant structure) | 99.5 | 230 | 3.0 |
| 32 | 18 | 4 | 10 | 15 | 0.05 (Slant structure) | 99.6 | 230 | 3.0 |
| 33 | 15 | 4 | 8 | 10 | 0.07 (Slant structure) | 99.5 | 240 | 3.5 |
| 34 | 15 | 3 | 5 | 10 | 0.07 (Slant structure) | 99.7 | 300 | 3.5 |
| 35 | 15 | 3 | 7 | 7 | 0.08 (Slant structure) | 99.7 | 180 | 2.5 |
| 36 | 10 | 7 | 7 | 7 | 0.07 (Slant structure) | 99.0 | 180 | 2.5 |
| 37 | 10 | 6 | 3 | 7 | 0.08 (Slant structure) | 99.3 | 190 | 2.7 |
| 38 | 8 | 6 | 2 | 7 | 0.09 (Slant structure) | 99.5 | 190 | 2.7 |
| 39* | 10 | 3 | 2 | 5 | — | 99.0 | 180 | 1.5 |

*Comparison

Figure 5:
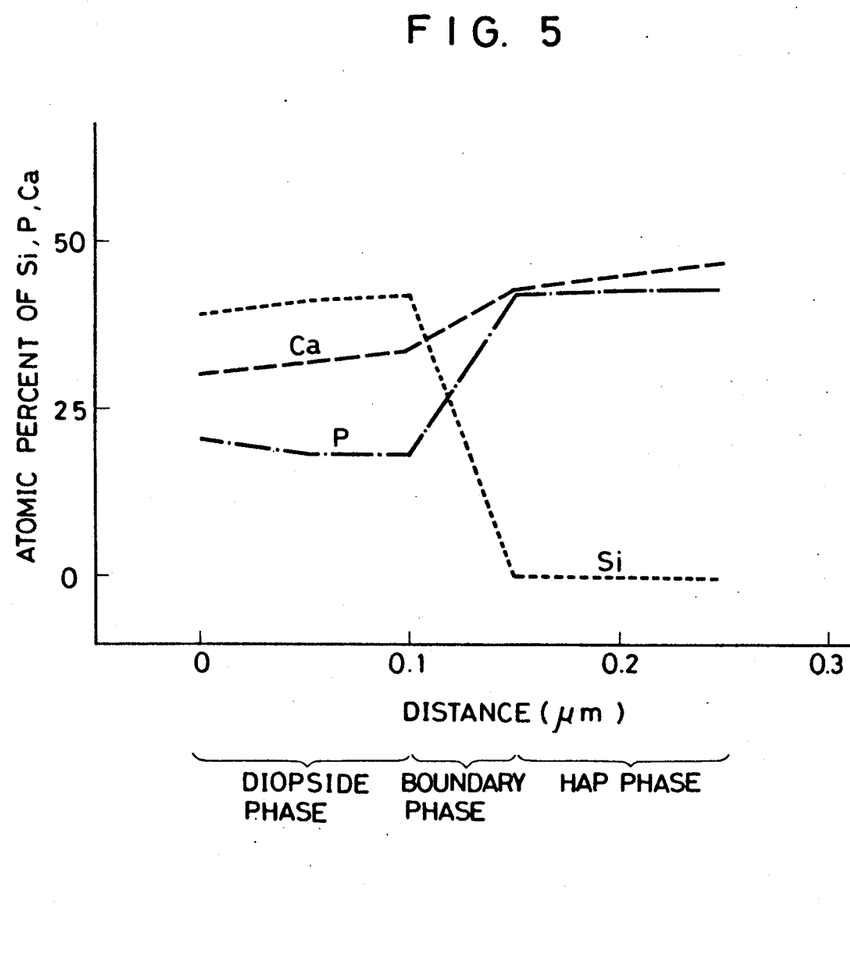
FIG. 5 is a diagram showing the results of analysis of a biomedical material under an electron microscope, plotting the atomic percents of Si, P and Ca in the diopside, boundary, and hydroxyapatite phases.

Sample No. 34 was analyzed by means of an analytical transmission electron microscope (ATEM). FIG. 5 shows the profiles of Si, Ca and P contents in atomic percent determined from X-ray peaks of Si, P and Ca. It is to be noted that O and H are excluded from the calculation of atom% of Si, Ca and P in the diagram of FIG. 5. It is seen from FIG. 5 that Ca, P and Si are contained in the grain boundary vitreous phase and that they have a graded concentration in the boundary phase.

EXAMPLE 8

To 80% by weight of a calcium phosphate material having a sintering temperature of 1150° C. was added 20% by weight of diopside having a sintering temperature of 1250° C. The mixture was sintered at 1300° C. for 2 hours, obtaining a diopside whisker-reinforced, sintered body. The sintered body showed well sintered state and had a flexural strength of 130 kg/cm² and a fracture toughness ($K_IC$) of 1.40.

EXAMPLE 9

Sintered bodies were prepared by the same procedure as in Example 8 except that the HAP and whisker-forming material used had the sintering temperatures shown in Table 8. For only sample No. 51, the mixture was sintered at 1260° C. The sintered state and physical properties of the sintered bodies are shown in Table 8.

The sintering temperature was determined by compacting a material to a density of 1.4 g/cm³, heating the compact at a rate of 20° C./min. by means of a thermodilatometer Model DL-1500 (manufactured by Shinku Rikou K.K.), and measuring the heating temperature at which a shrinkage factor of 5% was reached.

TABLE 8

| Material | Sample No. 51 | Sample No. 52 |
|---|---|---|
| HAP sinterable temperature (Tm) | 1070° C. | 950° C. |
| Whisker-forming material | | |
| Sinterable temperature (Tw) | 1250° C. | 1250° C. |
| Material | Diopside | Anorthite |
| Amount (wt %) | 20 | 20 |
| Sintering temperature | 1260° C. | 1300° C. |
| Tw-Tm | 180° C. | 300° C. |

TABLE 9

| | Sintered body | |
|---|---|---|
| | Sample No. 51 | Sample No. 52 |
| Whisker content (area %) | 18 | 15 |
| Matrix grain size (μm) | 3 | 10 |
| Whisker length (μm) | 4 | 4 |
| Whisker aspect ratio | 15 | 17 |
| Flexural strength (MPa) | 250 | 140 |
| Fracture toughness (MPa m) | 2.80 | 1.35 |

As seen from Tables 8 and 9, better results are obtained when the difference in sinterable temperature between the whisker-forming material and the calcium phosphate material (Tw - Tm) is in the range of from 50° to 400° C.

EXAMPLE 10

To 100 parts by weight of hydroxyapatite powder was added 50 parts by weight of silicon carbide whiskers having a length of 15 μm and an aspect ratio of 15. To 100 parts by weight of the mixture was added 40 parts by weight of a rubber. The mixture was milled in a laboratory plasto-mill for 30 minutes and then rolled into a plate through rollers under a pressure of 100 kg/cm². An SEM photomicrograph of a section of the plate showed that silicon carbide whiskers were oriented. The degree of orientation was 80%. The rolled plate was further shaped by hot pressing under a pressure of 200 kg/cm² and sintered at 1300° C., obtaining a sintered body having a degree of orientation of 80%, a flexural strength of 90 MPa, and a fracture toughness of 1.7 MP√am, which was ready for use as biomedical material.

It is to be noted that the degree of orientation of shaped and sintered articles was measured by powder X-ray diffraction with the peak intensity in the diffraction chart being expressed as I(00l)/I(nkl) in percent.

EXAMPLE 11

The procedure of Example 10 was repeated to prepare sintered bodies. Tricalcium phosphate sintering material, alumina whiskers, and binder were used in the proportion shown in Table 10. The mixture was milled, rolled, press shaped, and sintered under the conditions shown in Table 10. The degree of orientation, flexural strength and toughness of the sintered bodies are shown in Table 11.

TABLE 10

| Sample No. | Sintering¹ material (pbw) | Whiskers² (pbw) | Binder (pbw) | Rolling pressure (kg/cm²) | Press molding pressure (kg/cm²) | Sintering Temp. (°C.) |
|---|---|---|---|---|---|---|
| 61 | 100 | 50 | 25 | 100 | 200 | 1300 |
| 62 | 100 | 50 | 15 | 100 | 200 | 1300 |
| 63 | 100 | 50 | 5 | 100 | 200 | 1300 |
| 64 | 100 | 30 | 25 | 100 | 200 | 1300 |
| 65 | 100 | 30 | 35 | 100 | 200 | 1300 |
| 66 | 100 | 10 | 25 | 100 | 200 | 1300 |
| 67 | 100 | 10 | 35 | 100 | 200 | 1300 |

¹Tricalcium phosphate
²Alumina whiskers

TABLE 11

| Sample No. | Whisker content (area %) | Whisker length (μm) | Aspect ratio | Matrix grain size (μm) | Degree of orientation (%) | F.S. (MPa) | $K_1C$ (MPa $\sqrt{m}$) |
|---|---|---|---|---|---|---|---|
| 61 | 50 | 10 | 15 | 5 | 78 | 100 | 2.1 |
| 62 | 50 | 10 | 15 | 5 | 74 | 95 | 1.8 |
| 63 | 50 | 10 | 15 | 5 | 66 | 95 | 1.7 |
| 64 | 50 | 10 | 15 | 5 | 78 | 90 | 1.7 |
| 65 | 30 | 10 | 15 | 5 | 87 | 95 | 1.4 |
| 66 | 10 | 10 | 15 | 5 | 67 | 80 | 1.5 |
| 67 | 10 | 10 | 15 | 5 | 75 | 80 | 1.6 |

All the samples of Examples 4 to 11 exhibited good biological activity and affinity in an implanting test.

Although some preferred embodiments have been described, many modifications and variations may be made thereto in the light of the above teachings. It is therefore to be understood that within the scope of the appended claims, the invention may be practiced otherwise than as specifically described.

We claim:

1. A biomedical material in the form a sintered composite body comprising a crystalline calcium phosphate matrix having a grain size of 0.05 to 30 μm and inorganic whiskers having a length of 0.05 to 30 μm and an aspect ratio as defined by the length/diameter of from 1.2/1 to 100/1, the ratio of matrix grain size to whisker length ranging from 10/1 to 1/10 dispersed therein, the whiskers occupying 0.5 to 95% by area of a cross section of the sintered body, and the inorganic whiskers being selected from the group consisting of calcium silicate, calcium aluminosilicate, calcium magnesium silicate, calcium aluminate, and magnesium silicate whiskers.

2. The biomedical material of claim 1 wherein the crystalline calcium phosphate is tricalcium phosphate.

3. The biomedical material of claim 1 wherein the crystalline calcium phosphate is an apatite.

4. The biomedical material of claim 3 wherein the crystalline calcium phosphate is hydroxyapatite or fluoroapatite having an atomic calcium-to-phosphorus (Ca/P) ratio of from 165/100 to 175/100.

5. The biomedical material of claim 1 wherein the inorganic whiskers are selected from the group consisting of calcium aluminosilicate and calcium magnesium silicate whiskers.

6. The biomedical material of claim 5 wherein the inorganic whiskers are anorthite or diopside whiskers.

7. The biomedical material of claim 1, wherein an intermediate layer is present between the whiskers and the matrix grains, the intermediate layer containing at least one element present in either one or both of the whiskers and the matrix.

8. The biomedical material of claim 7 wherein the intermediate layer has a continuous or stepwise gradient of concentration and a thickness of up to 3 μm.

9. The biomedical material of claim 1 wherein the whiskers have a degree of orientation of at least 60%.

10. The biomedical material of claim 1, comprising 10–60% by weight of said inorganic whiskers per 100 parts by weight of said sintered body.

* * * * *